United States Patent
Hayashi et al.

(10) Patent No.: US 10,393,761 B2
(45) Date of Patent: Aug. 27, 2019

(54) BLOOD STATE EVALUATION DEVICE, BLOOD STATE EVALUATION SYSTEM, BLOOD STATE EVALUATION METHOD, AND PROGRAM

(71) Applicant: Sony Corporation, Tokyo (JP)

(72) Inventors: Yoshihito Hayashi, Chiba (JP); Yoichi Katsumoto, Tokyo (JP); Marcaurele Brun, Tokyo (JP)

(73) Assignee: Sony Corporation, Tokyo (JP)

( * ) Notice: Subject to any disclaimer, the term of this patent is extended or adjusted under 35 U.S.C. 154(b) by 591 days.

(21) Appl. No.: 14/778,277

(22) PCT Filed: Feb. 18, 2014

(86) PCT No.: PCT/JP2014/053704
§ 371 (c)(1),
(2) Date: Sep. 18, 2015

(87) PCT Pub. No.: WO2014/156370
PCT Pub. Date: Oct. 2, 2014

(65) Prior Publication Data
US 2016/0282366 A1 Sep. 29, 2016

(30) Foreign Application Priority Data
Mar. 29, 2013 (JP) .................. 2013-073508

(51) Int. Cl.
*G01N 33/86* (2006.01)
*G01N 27/02* (2006.01)
*G01N 33/49* (2006.01)

(52) U.S. Cl.
CPC .......... *G01N 33/86* (2013.01); *G01N 27/026* (2013.01); *G01N 33/4905* (2013.01)

(58) Field of Classification Search
None
See application file for complete search history.

(56) References Cited

U.S. PATENT DOCUMENTS

| 6,046,051 A | 4/2000 | Jina |
| 8,132,446 B2 | 3/2012 | Hayashi |
| (Continued) | | |

FOREIGN PATENT DOCUMENTS

| JP | 2004-501380 A | 1/2004 |
| JP | 2010-181400 A | 8/2010 |
| (Continued) | | |

OTHER PUBLICATIONS

U.S. Appl. No. 12/472,630, filed May 27, 2009, Hayashi.
U.S. Appl. No. 12/733,031, filed Feb. 3, 2010, Katsumoto et al.
U.S. Appl. No. 13/371,881, filed Feb. 13, 2012, Hayashi.
U.S. Appl. No. 14/760,238, filed Jul. 10, 2015, Hayashi et al.
U.S. Appl. No. 14/761,667, filed Jul. 17, 2015, Brun et al.
U.S. Appl. No. 14/763,980, filed Jul. 28, 2015, Brun et al.
U.S. Appl. No. 14/775,099, filed Sep. 11, 2015, Katsumoto et al.
(Continued)

*Primary Examiner* — Jill A Warden
*Assistant Examiner* — Brittany I Fisher
(74) *Attorney, Agent, or Firm* — Wolf, Greenfield & Sacks, P.C.

(57) ABSTRACT

A blood state evaluation device, blood state evaluation system, blood state evaluation method, and program that enable evaluation of the risk of thrombosis easily and precisely is provided. An electrical characteristic of blood being an evaluation target is chronologically measured in two or more frequencies or two or more frequency bands. On the basis of chronological change data of the measured electrical characteristic of the blood, a state of blood is evaluated.

12 Claims, 12 Drawing Sheets

(56) References Cited

U.S. PATENT DOCUMENTS

| | | |
|---|---|---|
| 8,478,546 B2 | 7/2013 | Katsumoto et al. |
| 9,097,635 B2 | 8/2015 | Hayashi |
| 2002/0019707 A1 | 2/2002 | Cohen et al. |
| 2009/0261987 A1* | 10/2009 | Sun ................ G01N 35/00732 340/870.07 |
| 2009/0293595 A1 | 12/2009 | Hayashi |
| 2010/0136606 A1 | 6/2010 | Katsumoto et al. |
| 2010/0305499 A1* | 12/2010 | Matsiev ................ A61B 5/145 604/67 |
| 2011/0119080 A1* | 5/2011 | Hayter ............... A61B 5/14532 705/2 |
| 2011/0203367 A1* | 8/2011 | Huang ............... G01N 33/4905 73/32 R |
| 2012/0035450 A1 | 2/2012 | Hayashi |
| 2012/0100601 A1* | 4/2012 | Simmons ........... A61B 5/14532 435/287.7 |
| 2012/0137753 A1 | 6/2012 | Hayashi |
| 2012/0238026 A1* | 9/2012 | Hayashi ................ G01N 33/86 436/69 |
| 2012/0329082 A1* | 12/2012 | Viola .................... B01L 3/5027 435/13 |
| 2013/0231947 A1* | 9/2013 | Shusterman ........ G06F 19/3443 705/2 |
| 2015/0323480 A1 | 11/2015 | Brun et al. |
| 2015/0346125 A1 | 12/2015 | Hayashi et al. |
| 2015/0377763 A1 | 12/2015 | Brun et al. |
| 2016/0011170 A1 | 1/2016 | Brun et al. |
| 2016/0018346 A1 | 1/2016 | Hayashi et al. |
| 2016/0025610 A1 | 1/2016 | Katsumoto et al. |
| 2016/0282366 A1 | 9/2016 | Hayashi et al. |
| 2016/0299124 A1 | 10/2016 | Brun et al. |

FOREIGN PATENT DOCUMENTS

| | | |
|---|---|---|
| JP | 2011-257403 A | 12/2011 |
| JP | 2012-194087 A | 10/2012 |
| WO | WO 2010/079845 A1 | 7/2010 |

OTHER PUBLICATIONS

Watanabe et al., Predicitive blood coagulation markers for early diagnosis of venous thromboembolism after total knee joint replacement,Thrombosis Research, 2011; 128:e137-43.

Japanese Office Action dated Apr. 16, 2019 in connection with Japanese Application No. 2018-121826 and English translation thereof.

Hayashi et al., An Approach for Risk Assessment of Venous Thrombosis Using Dielectric Spectroscopy [Jomyaku Kessensho no Risk Hyoka ni Muketa Yuden Bunkoho ni yoru Approach] Dai 32 Kai Japanese Society of Biorheology Nenkai Program Shorokushu. May 18, 2009; p. 75.

Irimajiri et al., Dielectric monitoring of rouleaux formation in human whole blood: a feasibility study, Biochimica et Biophysica Acta, 1996, 1290:207-9.

Irimajiri et al., Hemagglutination (rouleau formation) judging from dielectric behavior of the whole blood [Zenketsu no Yuden Kyodo kara Mita Sekkekkyu Gyoshu (Rensen Keisei)],Biotechnology, 2000;78(5):162-5.

Uchimura et al., Measurement of Blood Coagulation by Dielectric Spectroscopy and Its Application to Diabetes [Yuden Bunkoho ni yoru Ketsueki Gyoko Sokutei to Tonyobyo eno Oyo] The $1^{st}$ International Symposium of Biorheolog,, The $33^{rd}$ Annual Meeting of the Japanese Society of Biorheology Program-shu. May 28, 2010; p. 99.

\* cited by examiner

BLOOD STATE EVALUATION DEVICE, BLOOD STATE EVALUATION SYSTEM, BLOOD STATE EVALUATION METHOD, AND PROGRAM

CROSS-REFERENCE TO RELATED APPLICATIONS

This application is a National Stage of International Application No. PCT/JP2014/053704, filed in the Japanese Patent Office as a Receiving office on Feb. 18, 2014, which claims priority to Japanese Patent Application Number 2013-073508, filed in the Japanese Patent Office on Mar. 29, 2013.

TECHNICAL FIELD

The present technology relates to a blood state evaluation device, a blood state evaluation system, a blood state evaluation method, and a program. More specifically, the present technology relates to a technology for evaluating a state of blood from a chronological change in an electrical characteristic.

BACKGROUND ART

Anti-platelet aggregation agents or anti-coagulant agents are prophylactically administered to patients or healthy persons who have thrombosis risks. Examples of the patients having thrombus formation risks include patients with diabetes, arteriosclerosis, cancer, heart disease, and respiratory disease; perioperative patients; and patients taking immunosuppressants. Also, examples of the healthy persons having thrombus risks include pregnant women and elderly people. As the anti-platelet aggregation agents, acetylsalicylic acid and the like are used; and as the anti-coagulant agents, warfarin, heparin, activated blood coagulation factor Xa inhibitors, direct thrombin inhibitors, and the like are used.

The prophylactic administration of anti-platelet aggregation agents and anti-coagulant agents against thrombosis has the side effect that an excessively high administered dose increases a bleeding risk. In order to obtain a sufficient prophylactic effect while inhibiting this side effect, an administration management becomes important in which blood coagulability of an administered subject is timely evaluated, and the drug and dose to be administered are appropriately selected and determined.

A method for a blood coagulability test for managing drug administration includes the prothrombin time-international normalized ratio (PT-INR), the activated partial thromboplastin time (APTT), and the like. Also, a method for a platelet aggregation test includes adding a substance that induces aggregation of platelet to platelet rich plasma (PRP) obtained by centrifuging blood, and measuring a change in transmitted light levels or absorbance associated with the aggregation to determine good or poor in aggregation capacity.

Meanwhile, as a method for a venous thromboembolism (VTE) test, mainly, ultrasonography is used for deep vein thrombosis (DVT), and computed tomography (CT) is used for pulmonary embolism (PE), for example. In the related art, a report has been presented on a study to predict venous thromboembolism (VTE) that occurs as a side effect of artificial knee joint replacement by measuring a biomarker (Non-Patent Literature 1).

CITATION LIST

Non-Patent Literature

Non-Patent Literature 1: H. Watanabe, and ten others, "Predictive blood coagulation markers for early diagnosis of venous thromboembolism after total knee joint replacement", Thrombosis Research, 2011, Vol. 128, pp. 137-143.

SUMMARY OF INVENTION

Technical Problem

However, known blood coagulability tests such as PT-INR and APTT substantially evaluate only the bleeding risk associated with reduction in blood coagulability caused by excess administration of anti-coagulant agents, and cannot evaluate the thrombus risk associated with enhancement in blood coagulability. Also, the existing platelet aggregation test using PRP may require a centrifugation process. This may cause platelet to be activated during this process, thereby inhibiting accurate test results from being obtained. Furthermore, the operation is complicated.

On the other hand, image diagnosis by ultrasonography or computed tomography is highly precise and accurate, enabling definite diagnosis. However, such tests need time and effort, and such image diagnosis cannot evaluate the "risk" of whether a thrombus will occur in the future, before a thrombus occurs, because such image diagnosis fundamentally detects a thrombus that has already occurred. Furthermore, a method using a biomarker does not have sufficient sensitivity and specificity. For example, a study using a D-meter has a sensitivity of 75% and a specificity of 63%, and a study using an e-XDP has a sensitivity of 75% and a specificity of 59%.

Accordingly, the present disclosure mainly aims to provide a blood state evaluation device, blood state evaluation system, blood state evaluation method, and program that enable evaluation of the risk of thrombosis easily and precisely.

Solution to Problem

As techniques that can evaluate the degree of enhancement of blood coagulation easily and accurately, the present inventors have proposed techniques for performing dielectric measurement of the process of blood coagulation (JP 2010-181400A and JP 2012-194087A). These techniques are methods for filling a sample part with blood, the sample part being like a capacitor including a pair of electrodes and the like, and measuring changes in permittivity associated with the process of blood coagulation by applying an alternating field thereto.

As a blood specimen, a blood specimen obtained by collecting blood from a vein by using citric acid, for example, as an anti-coagulant agent is used. Immediately before the start of measurement, an aqueous solution of calcium chloride is added so as to release the anti-coagulant function of citric acid, causing the reaction of blood coagulation to progress. Then, by analyzing complex permittivity spectrum obtained by the measurement according to a predetermined algorithm, enhancement or reduction of blood coagulability such as a blood coagulation time can be evaluated.

Accordingly, the present inventors have intensely considered and tested a method for evaluating the risk of venous thromboembolism (VTE) by using data of an electrical characteristic of blood obtained through measurement using an electrical characteristic measurement device such as the above-described dielectric coagulometer, and have made the present invention.

That is, a blood state evaluation device according to the present disclosure includes at least an evaluation unit configured to evaluate a state of blood on the basis of chronological change data of an electrical characteristic of the blood in two or more frequencies or frequency bands.

The evaluation unit may extract at least one feature point from the chronological change data of the electrical characteristic.

In this case, the at least one feature point may be a change amount $\delta E$ (=$E(f_x,t_y)/E(f_x,t_a)$) in an electrical characteristic value E in a given frequency $f_x$ from a reference time $t_a$ to a given time $t_y$, for example.

The evaluation unit may also digitalize the chronological change data of the electrical characteristic.

In this case, the evaluation unit may evaluate the state of the blood by comparing a determination value calculated from the chronological change data of the electrical characteristic with a predetermined threshold.

The evaluation unit may evaluate the state of the blood by an increase and/or a decrease in an electrical characteristic value E in a given frequency $f_x$ on the basis of the chronological change data of the electrical characteristic.

Meanwhile, the electrical characteristic may be at least one kind of values selected from impedance, conductance, admittance, capacitance, permittivity, conductivity, phase angle, and a quantity obtained by conversing such a value into a quantity of electricity.

In addition, the evaluation unit may evaluate a coagulation state of the blood.

Further, a measurement unit configured to chronologically measure the electrical characteristic of blood being an evaluation target, in a particular frequency or frequency band may be provided.

A blood state evaluation system according to the present disclosure includes: an electrical characteristic measurement device including a measurement unit that chronologically measures an electrical characteristic of blood being an evaluation target, in a particular frequency or frequency band; and a blood state evaluation device including an evaluation unit that evaluates a state of the blood on the basis of chronological change data in two or more frequencies or frequency bands from among electrical characteristics measured by the electrical characteristic measurement device.

The blood state evaluation system may further include a server including an information storage unit that stores a result of measurement in the permittivity measurement device and/or a result of evaluation in the blood state evaluation device, in which the server may be connected to the permittivity measurement device and/or the blood state evaluation device through a network.

A blood state evaluation method according to the present disclosure includes: an electrical characteristic measurement step of chronologically measuring an electrical characteristic of blood being an evaluation target in a particular frequency or frequency band; and a blood state evaluation step of evaluating a state of the blood on the basis of chronological change data in two or more frequencies or frequency bands from among electrical characteristics measured in the electrical characteristic measurement step.

A program according to the present disclosure is a program for causing a computer to execute an evaluation function of evaluating a state of blood on the basis of chronological change data of an electrical characteristic of the blood in two or more frequencies or frequency bands.

Advantageous Effects of Invention

According to the present disclosure, since the blood state is evaluated on the basis of chronological change data of an electrical characteristic, it becomes possible to evaluate the risk of thrombosis easily and precisely.

DESCRIPTION OF EMBODIMENTS

Embodiments for implementing the present disclosure will be described in detail below with reference to the appended drawings. Note that the present disclosure is not limited to each embodiment described below. The description will be made in the following order.

1. First Embodiment
   (Example of Blood State Evaluation Device that Evaluates Thrombosis Risk from Chronological Change in Electrical Characteristic)
2. Second Embodiment
   (Example of Blood State Evaluation System)

<1. First Embodiment>

First, a blood state evaluation device according to a first embodiment of the present disclosure will be described. As a risk factor of venous thromboembolism (VTE), "stasis of blood flow", "vascular endothelial injury", and "enhancement of blood coagulability" are known and are called "Virchow's triad".

Examples of general risk factors of thrombosis include aging, obesity, protracted bed rest, maintenance of the same posture, and dehydration. Examples of risk factors relating to disease include congenital hypercoagulability, malignant tumor, inflammatory bowel disease, and nephrotic syndrome. Furthermore, there are various risk factors such as those relating to medicine including steroid and hormone drug, and those relating to medical treatment including surgery and catheterization. Among these risk factors, in particular, medical treatment such as artificial knee joint replacement is known to have a high risk of thrombosis.

Meanwhile, even with the above-described risk factor(s), it differs significantly among individuals whether venous thromboembolism (VTE) really occurs. From such reasons, it is desirable to achieve a method that enables prediction of the thrombosis risk of each person by a simple method such as a blood test.

Figure 1:
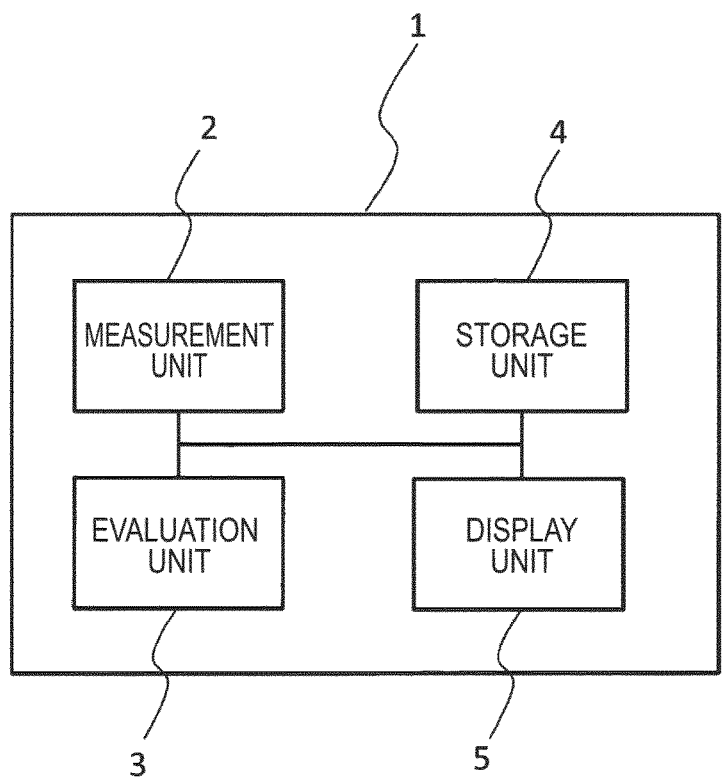
FIG. 1 is a block diagram illustrating a configuration example of a blood state evaluation device according to a first embodiment of the present disclosure.

Accordingly, on the basis of chronological change data of an electrical characteristic of blood in two or more frequencies or two or more frequency bands, the blood state evaluation device according to the present embodiment evaluates the state of blood, and predicts the thrombosis risk from the result. FIG. 1 is a block diagram illustrating a configuration example of the blood state evaluation device according to the present embodiment. As illustrated in FIG. 1, a blood state evaluation device 1 according to the present embodiment includes a measurement unit 2, an evaluation unit 3, a storage unit 4, a display unit 5, and the like.

[Measurement Unit 2]

The measurement unit 2 chronologically measures an electrical characteristic of blood, which is an evaluation target, in a particular frequency or frequency band. The electrical characteristic measured by the measurement unit 2 includes, for example, impedance, conductance, admittance, capacitance, permittivity, conductivity, phase angle, and a quantity obtained by converting such a value into a quantity of electricity. The blood state evaluation device 1 according to the present embodiment can conduct evaluation by using one of these electrical characteristics, but may also use two or more electrical characteristics.

A configuration of the measurement unit 2 is not particularly limited, and may be appropriately determined depending on the electrical characteristic to be measured. For example, when an alternating voltage is applied between a pair of electrodes provided in a sample container to measure the impedance and permittivity of blood, an impedance analyzer and a network analyzer can also be used as the measurement unit 2.

Note that the measurement unit 2 may conduct measurement only in a frequency or frequency band used by the later-described evaluation unit 3, but may also measure the electrical characteristic in a wide band by changing frequencies so as to extract the frequency or frequency band used for evaluation from the obtained spectrum.

[Evaluation Unit 3]

The evaluation unit 3 evaluates the state of blood on the basis of chronological change data in two or more frequencies or two or more frequency bands from the electrical characteristic measured by the above-described measurement unit 2. Examples of the states of blood as the evaluation target include blood coagulation state, aggregation state, solidification state, and blood clot shrinkage state.

Evaluation by the evaluation unit 3 may be conducted by employing a method for extracting feature points from chronological change data of the electrical characteristic, a method for digitizing chronological change data of the electrical characteristic, a method for comparing a determination value calculated from chronological change data of the electrical characteristic, with a predetermined threshold, and the like. Alternatively, the evaluation unit 3 may evaluate the state of blood by increase and/or decrease in an electrical characteristic value E in a given frequency $f_x$ on the basis of chronological change data of the electrical characteristic, for example. Note that the evaluation method in the evaluation unit 3 is not limited to the above-described methods and various methods may be employed.

[Storage Unit 4]

The storage unit 4 stores chronological change data of the electrical characteristic of blood, which has been measured by the measurement unit 2, the result of evaluation in the evaluation unit 3, and the like. The storage unit 4 is configured from a hard disk, for example.

[Display Unit 5]

The display unit 5 displays chronological change data of the electrical characteristic of blood, which has been measured by the measurement unit 2, the result of evaluation in the evaluation unit 3, and the like. The display unit 5 may have any configuration by which these can be viewed.

[Operation]

Next, the operation of the above-described blood state evaluation device 1, that is, a method for evaluating the state of blood and predicting the thrombosis risk by using the blood state evaluation device 1 will be described.

(Electrical Characteristic Measurement Step)

In the blood state evaluation device 1 according to the present embodiment, first, in the measurement unit 2, the electrical characteristic of blood being an evaluation target is measured chronologically in a particular frequency or frequency band. In this event, conditions for measuring the electrical characteristic are not limited to particular conditions, and can be set as appropriate depending on the kind of electrical characteristic as long as the blood being the evaluation target is not altered.

The measurement may be conducted in a frequency or frequency band that is used in an evaluation step, or the electrical characteristic may be measured in a wide band including all the frequencies and frequency bands that are used. In this case, from the obtained spectrum, a frequency or frequency band used for evaluation is extracted in the evaluation unit 3.

(Blood State Evaluation Step)

Figure 2A:
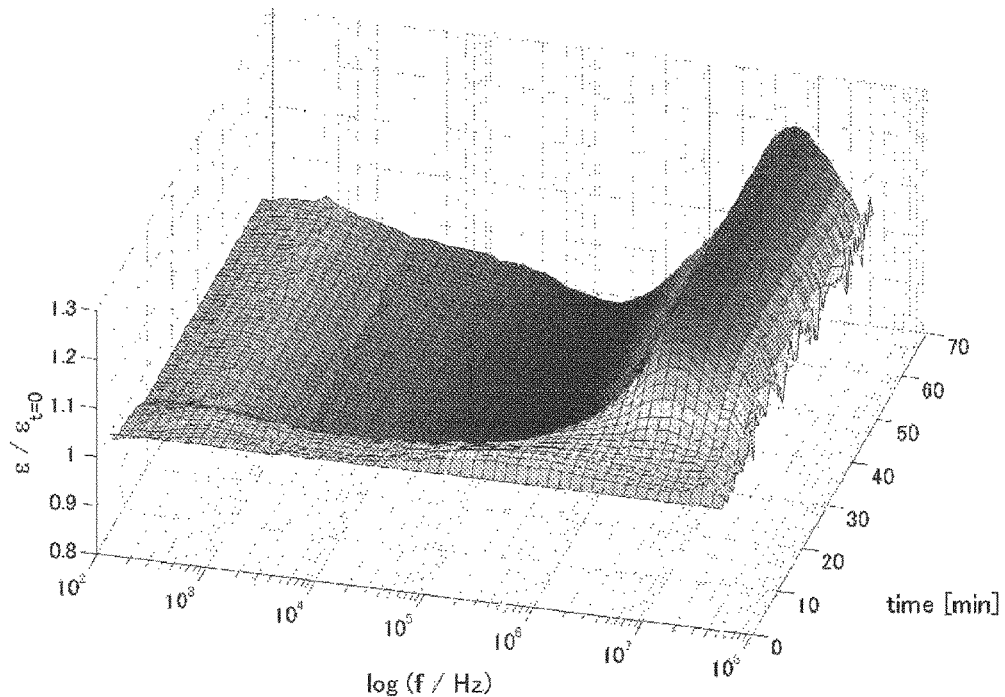
FIG. 2A is chronological change data of permittivity (change amount $\delta\varepsilon$ of a real part of complex permittivity) of blood of thrombosis.
Figure 2B:
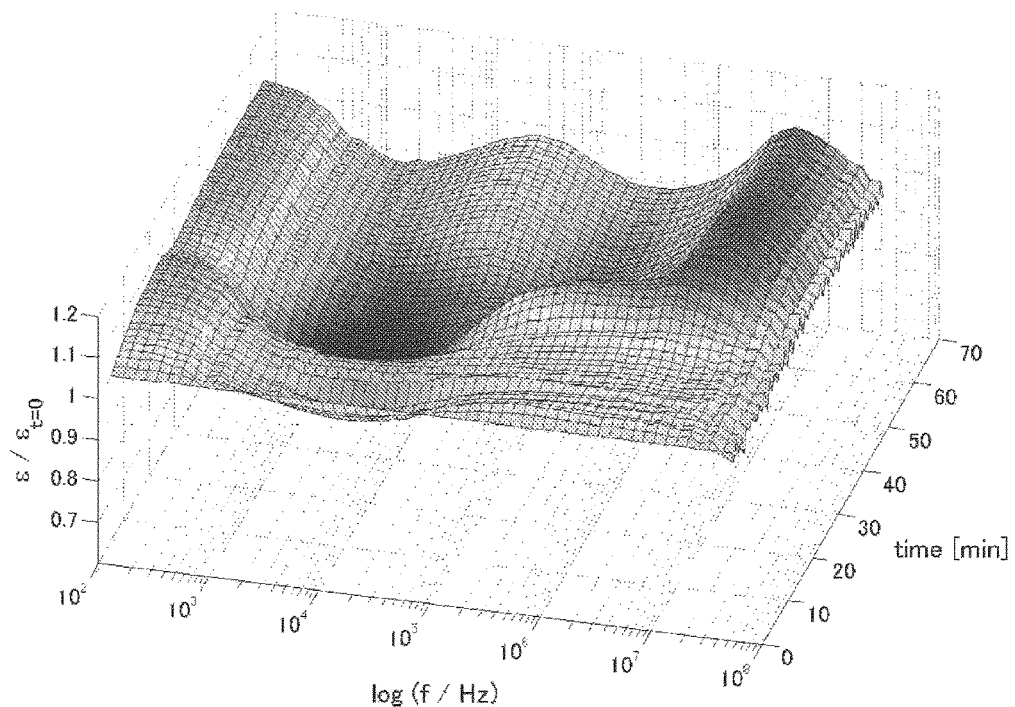
FIG. 2B is chronological change data of permittivity (change amount $\delta\varepsilon$ of a real part of complex permittivity) of blood of a healthy person.
Figure 2C:
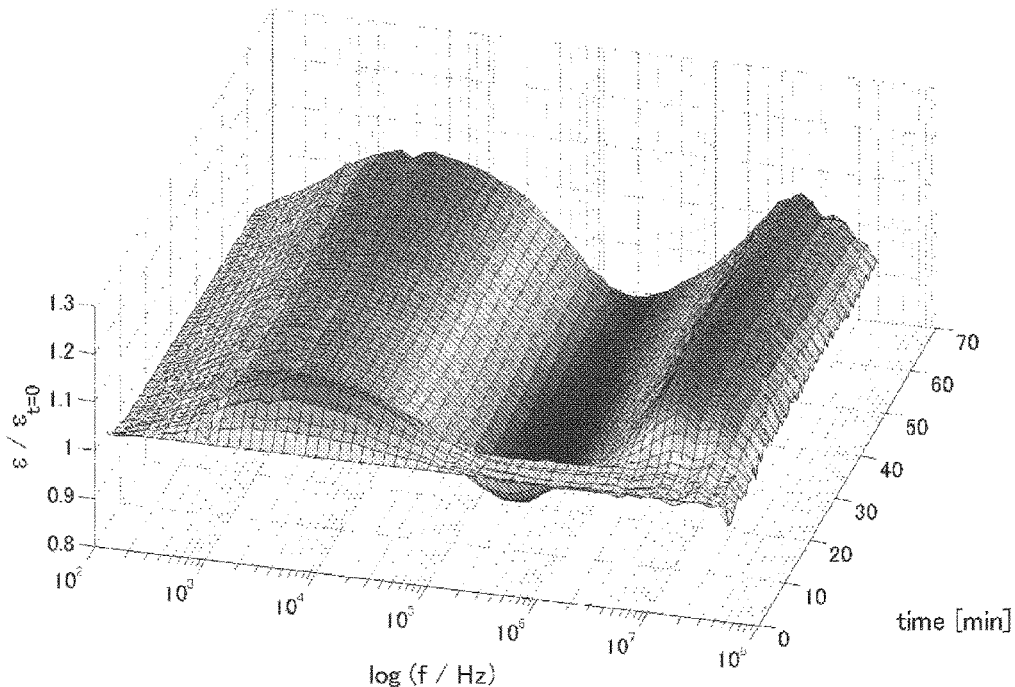
FIG. 2C is chronological change data of permittivity (change amount $\delta\varepsilon$ of a real part of complex permittivity) of blood of elevated blood sedimentation.
Figure 3A:
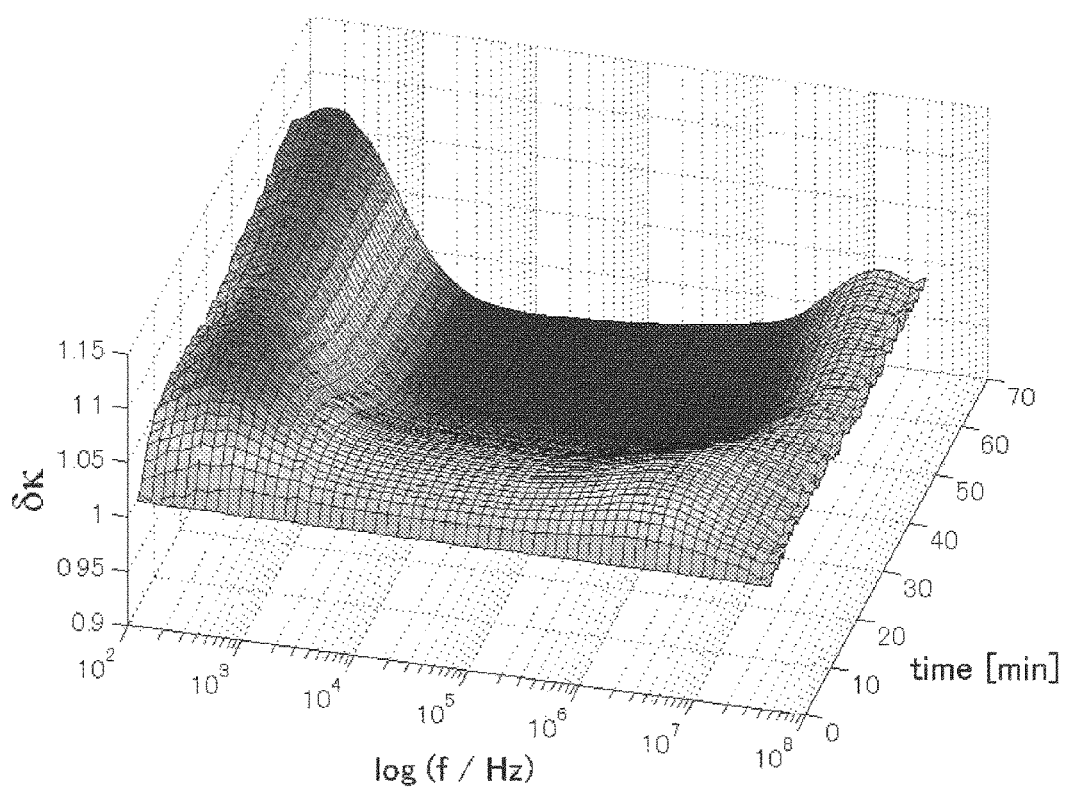
FIG. 3A is chronological change data of an electrical conductivity (change amount $\delta\kappa$) of blood having an erythrocyte sedimentation rate in a normal range.
Figure 3B:
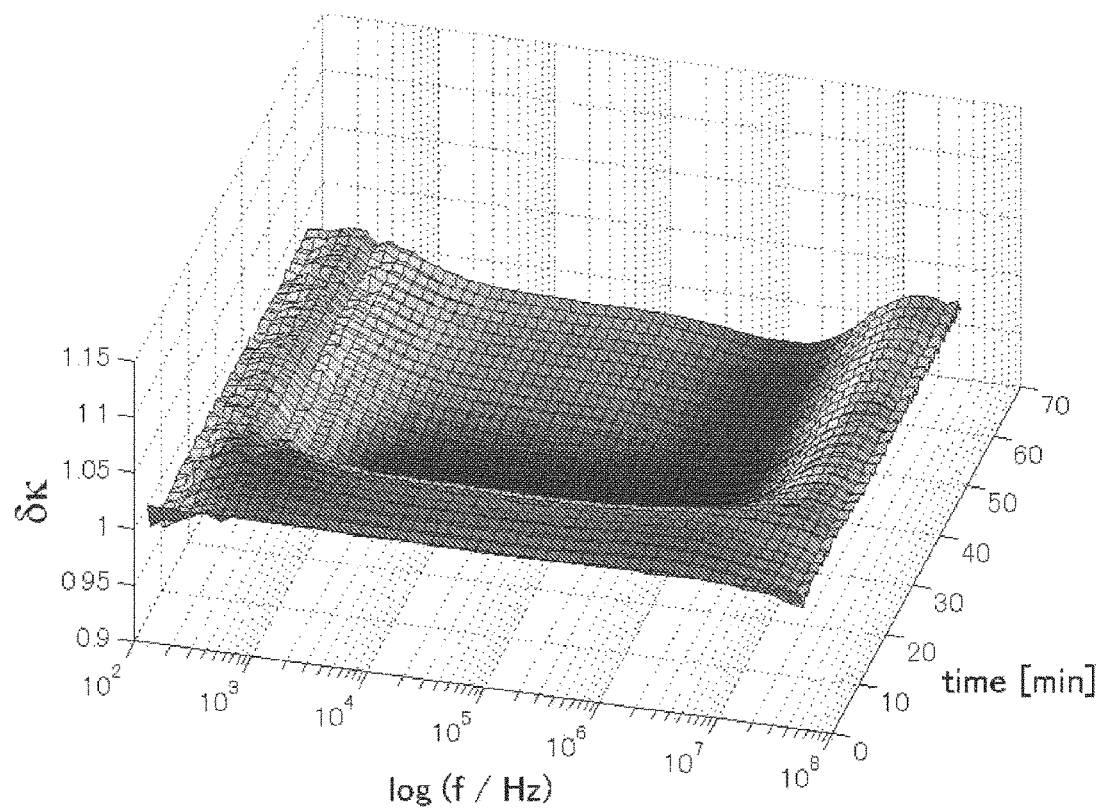
FIG. 3B is chronological change data of an electrical conductivity (change amount $\delta\kappa$) of blood having an erythrocyte sedimentation rate in a normal range.
Figure 3C:
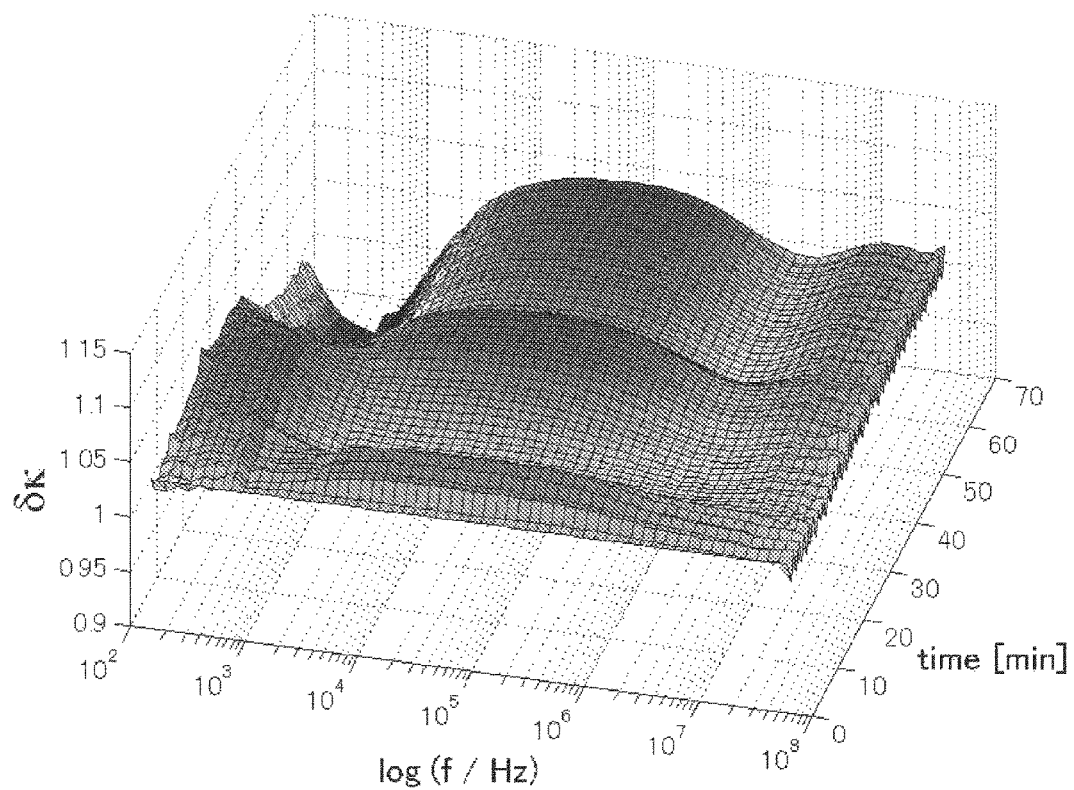
FIG. 3C is chronological change data of an electrical conductivity (change amount $\delta\kappa$) of blood having an erythrocyte sedimentation rate in an abnormal range.
Figure 3D:
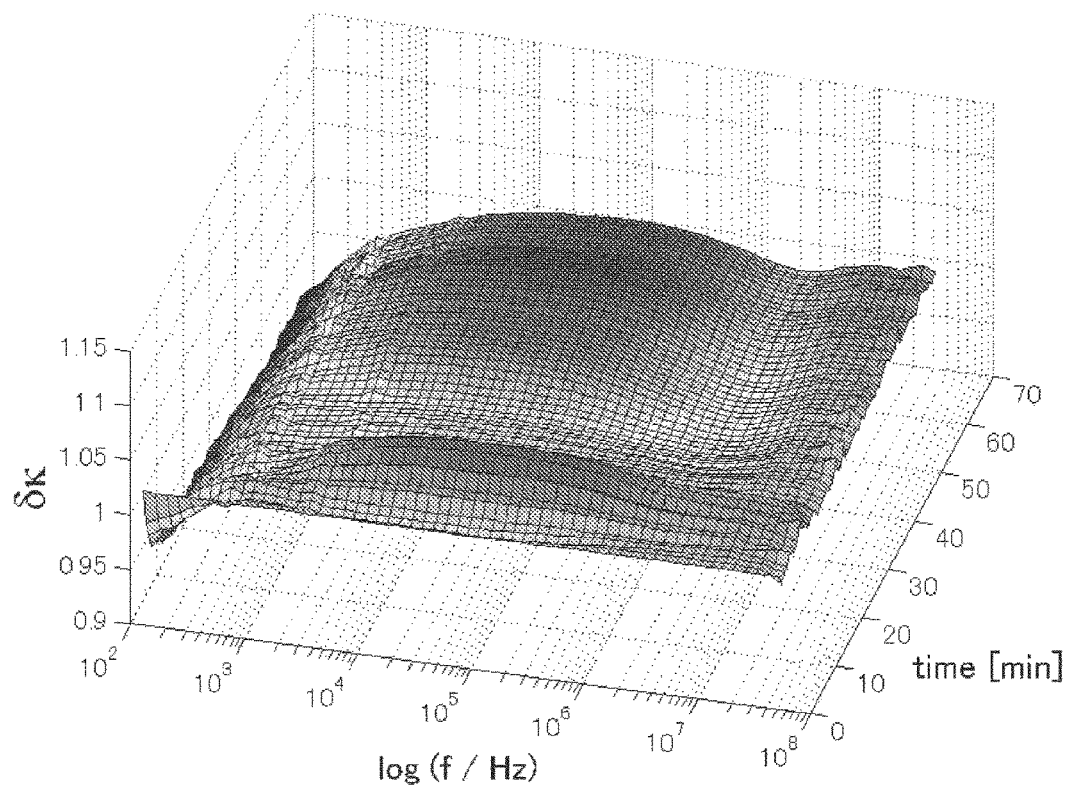
FIG. 3D is chronological change data of an electrical conductivity (change amount $\delta\kappa$) of blood having an erythrocyte sedimentation rate in an abnormal range.

Next, using the electrical characteristic of blood obtained through the electrical characteristic measurement step, the state of blood being the target is evaluated in the evaluation unit 3. For example, in a case where the electrical characteristic is permittivity, chronological change data as illustrated in FIGS. 2A to 2C is obtained. Here, the chronological change data illustrated in FIGS. 2A to 2C shows change amounts $\delta\varepsilon(=\varepsilon/\varepsilon_{t=0})$ in real parts of complex permittivity of blood of thrombosis (FIG. 2A), blood of a healthy person (FIG. 2B), and blood of elevated blood sedimentation (FIG. 2C). The data shows values obtained by measuring impedance in a frequency region of 100 Hz to 40 MHz under a condition of temperature being 37° C. for 60 minutes with 1-minute measurement intervals.

As illustrated in FIG. 2A, as for the blood of thrombosis, permittivity around 10 MHz explicitly increases due to blood coagulation. Meanwhile, as illustrated in FIG. 2B, as for the blood of the healthy person, in addition to this increase, permittivity increases due to hemagglutination around 1 MHz and decreases thereafter. In addition, as illustrated in FIG. 2C, as for the blood of elevated blood sedimentation, permittivity increases indicating blood sedimentation around 2.5 kHz. By using these features, it becomes possible to predict the thrombus risk.

In the above manner, the features of obtained chronological change data of the electrical characteristic differ depending on the state of blood. The use of the features makes it possible to predict the thrombosis risk. Specifically, it is possible to evaluate the state of the blood by using increase and/or decrease in the electrical characteristic value E in the given frequency $f_x$ on the basis of chronological change data of the electrical characteristic.

For example, in a case where the electrical characteristic is a change in permittivity associated with blood coagulation, as the overall trend, as for blood positive for thrombosis, in a high frequency band around 10 MHz (3 to 30 MHz), increase in permittivity associated with blood coagulation becomes obvious. In addition, as for the blood positive for thrombosis, in some cases, increase in permittivity may be seen due to erythrocyte rouleaux formation in about 12 minutes from the addition of an aqueous solution of calcium for blood coagulation, in a middle frequency band around 1 MHz (higher than or equal to 100 kHz and lower than 3 MHz).

However, the blood positive to thrombosis has a smaller increase in permittivity associated with blood coagulation in a middle frequency band around 1 MHz than in a high frequency band around 10 MHz. Immediately after this small increase, permittivity decreases significantly, and after that, permittivity tends to be a substantially constant low value. In addition, the blood positive for thrombosis tends to have a significant decrease in permittivity associated with blood coagulation in a low frequency band of higher than or equal to 1 kHz and lower than 100 kHz.

On the other hand, the blood negative for thrombosis has the following two distinctive patterns. A first pattern is a case where the increase in permittivity can be seen in a low frequency band, unlikely in positive blood. A second pattern is a case where the increase in permittivity associated with blood coagulation and the following decrease are observed separately from the increase in permittivity due to erythrocyte rouleaux formation that is seen in about 12 minutes from the addition of an aqueous solution of calcium, as described above, in a middle frequency band. The second pattern that is distinctive in the middle frequency band may be a distinctive change as in the blood of the healthy person.

The blood state evaluation device 1 according to the present embodiment evaluates the thrombosis risk using this feature. Specifically, in a case where permittivity obviously increases in a high frequency band (3 to 30 MHz) and hardly changes or significantly decreases in a middle frequency band (higher than or equal to 100 kHz and lower than 3 MHz) and a low frequency band (higher than or equal to 1 kHz and lower than 100 kHz), the thrombosis risk is evaluated to be high. On the other hand, in a case where permittivity explicitly increases in the middle frequency band (higher than or equal to 100 kHz and lower than 3 MHz), or in a case where permittivity has a high value in the low frequency band (higher than or equal to 1 kHz and lower than 100 kHz) even when blood coagulation occurs, the thrombosis risk is evaluated to be low.

The evaluation of the blood state can alternatively be conducted by a method for extracting at least one feature point from chronological change data of the electrical characteristic. The feature point(s) in this case can be set as a change amount $\delta E$ $(=E(f_x,t_y)/E(f_x,t_a))$ in the electrical characteristic value E from a reference time $t_a$ to a given time $t_y$ in the given frequency $f_x$.

Alternatively, the evaluation may be conducted by digitalizing chronological change data of the electrical characteristic. For example, in a case where the electrical characteristic is a change in permittivity associated with blood coagulation, the evaluation may be conducted by using a determination value $p_1$ calculated from the following formula 1. This determination value $p_1$ is calculated from a change amount $\delta \in (f_1,t_1)$ in permittivity in a first frequency $f_1$ at a first time $t_1$, a change amount $\delta \in (f_2,t_2)$ in permittivity in a second frequency $f_2$ at a second time $t_2$, and a change $\delta \epsilon (f_3,t_3)$ in permittivity in a third frequency $f_3$ at a third time $t_3$. Note that $\delta \epsilon (f,t)\}=\epsilon (f,t)/\epsilon (f,t=0)$ is a ratio between the measured permittivity and time 0 (before the initiation of a blood coagulation reaction). This applies to the following determination formula.

$$p_1=\{\delta\epsilon(f_1,t_1)\}^2\times\delta\epsilon(f_2,t_2)/\{\delta\in(f_3,t_3)\}^2 \qquad [\text{Math 1}]$$

wherein $f_1<f_2<f_3$, $t_1<t_2$, and $t_1<t_3$.

The evaluation can alternatively conducted using a determination value $p_2$ calculated from the following formula 2. Note that a in the following formula 2 is a given constant. The following formula 2 is an formula obtained empirically. The present inventors have found that the determination value $p_2$ calculated from the formula 2 is valid for evaluation of pulmonary embolism (PE), which is more serious than venous thromboembolism (VTE).

$$p_2=100\times[a-\delta\epsilon(f_1,t_1)\times\delta\epsilon(f_2,t_2)/\{\delta\in(f_3,t_3)\}^2]^2 \qquad [\text{Math 2}]$$

wherein $f_1<f_2<f_3$ and $t_1\leq t_2\leq t_3$.

Furthermore, although the determination value is calculated by using three-point frequency data of the formulas 1 and 2, the evaluation is also possible by using a determination value $p_3$ calculated from two-point frequency data from the following formula 3.

$$p_3=\{\delta\epsilon(f_1,t_1)\}^2/\{\delta\epsilon(f_2,t_2)\}^2 \qquad [\text{Math 3}]$$

wherein $f_1<f_2$ and $t_1<t_2$.

By comparing the determination values $p_1$, $p_2$, and $p_3$ calculated from the formulas 1 to 3 with a predetermined threshold, it is possible to evaluate the blood state easily.

The above-described blood state evaluation step can be conducted by creating and mounting, in a personal computer for example, a computer program for achieving the functions of an information processing apparatus. Such a computer program may also be stored in a recording medium such as a magnetic disk, an optical disc, a magneto-optical disk, or a flash memory, or may be distributed through a network.

Note that the electrical characteristic data measured by the measurement unit 2 may also be stored in the storage unit 4 and may be displayed on the display unit 5 as necessary, in addition to being evaluated by being sent to the evaluation unit 3. The evaluation result obtained in the evaluation unit 3 may be stored in the storage unit 4 and may be displayed on the display unit 5 as necessary.

The above-described electrical characteristic measurement step and blood state evaluation step are not necessarily performed consecutively. The evaluation may be conducted by storing data obtained by the measurement unit 2 in the storage unit 4 and by reading out the data by the evaluation unit 3 from the storage unit 4, as appropriate.

In addition, although the blood state evaluation device 1 illustrated in FIG. 1 includes the measurement unit 2, the storage unit 4, and the display unit 5, the blood state evaluation device 1 includes at least the evaluation unit 3. Furthermore, in the present embodiment, the case where the electrical characteristic is permittivity is described as an example, but the present disclosure is not limited to a method using permittivity. Similarly, the evaluation is possible by using other electrical characteristics such as impedance, admittance, and capacitance.

FIGS. 3A to 3D are each chronological change data of an electrical conductivity δκ of blood measured in a range of 100 Hz to 40 MHz. Referring to a frequency band of 5 kHz to 1 MHz, blood having an erythrocyte sedimentation rate in a normal range illustrated in FIGS. 3A and 3B has a low electrical conductivity δκ on a long-time side in association with blood coagulation. On the other hand, blood having an erythrocyte sedimentation rate in an abnormal range illustrated in FIGS. 3C and 3D has a high electrical conductivity δκ on a long-time side in a frequency band of 5 kHz to 1 MHz. By use of this characteristic, even when the electrical conductivity δκ is used, it is possible to evaluate the thrombus risk highly precisely.

As specifically described above, in the blood state evaluation device according to the present embodiment, the blood state is evaluated on the basis of chronological change data of the electrical characteristic. Accordingly, a simple blood test enables evaluation of the thrombosis risk at a high sensitivity and a high specificity. Thus, the load on the medical site can be reduced.

<2. Second Embodiment>

Figure 4:
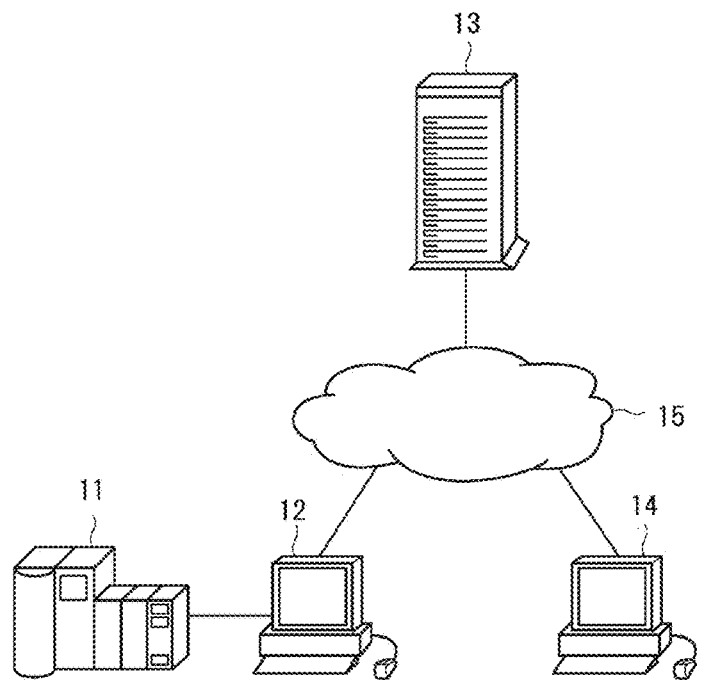
FIG. 4 is a diagram illustrating a schematic configuration of a blood state evaluation system according to a second embodiment of the present disclosure.

Next, a blood state evaluation system according to a second embodiment of the present disclosure will be described. FIG. 4 is a diagram illustrating a schematic configuration of the blood state evaluation system according to the present embodiment. In the blood state evaluation device according to the first embodiment described above, the electrical characteristic is measured and the blood state is evaluated within the device. However, the blood state can be evaluated in an information processing device connected to an electrical characteristic measurement device.

That is, as illustrated in FIG. 4, the blood state evaluation system according to the present embodiment includes an electrical characteristic measurement device 11 and an information processing device 12. The blood state evaluation system according to the present embodiment may be connected to a server 13, a display device 14, and the like, as necessary.

[Electrical Characteristic Measurement Device 11]

The electrical characteristic measurement device 11 includes a measurement unit that applies a voltage between a pair of electrodes provided in a sample container to be filled with blood being the measurement target, and to chronologically measure an electrical characteristic of the blood in a particular frequency or frequency band. A configuration of the electrical characteristic measurement device 11 is not particularly limited, and may be appropriately determined in accordance with the electrical characteristic to be measured. For example, when an alternating voltage is applied between a pair of electrodes to measure the impedance and permittivity of blood, an impedance analyzer and a network analyzer can also be used.

[Information Processing Device 12]

The information processing device 12 is connected to the electrical characteristic measurement device 11, and includes an evaluation unit that evaluates the state of blood on the basis of chronological change data in two or more frequencies or frequency bands from among the electrical characteristics measured by the electrical characteristic measurement device 11. Note that a specific configuration and operation of the evaluation unit are the same as in the above-described first embodiment.

[Server 13]

The server 13 is connected to the information processing device 12 and the display device 14 through a network 15, and includes an information storage unit, for example. Further, the server 13 manages various kinds of data uploaded from the information processing device 12, and outputs data to the display device 14 and the information processing device 12 in response to a request.

[Display Device 14]

The display device 14 displays chronological change data of the electrical characteristic of blood, which has been measured by the electrical characteristic measurement device 11, the result of evaluation in the evaluation unit of the information processing device 12, and the like. The display device 14 may be provided with an information input unit so that a user can select and input data to be displayed. In this case, information inputted by the user is transmitted to the server 13 and the information processing device 12 through the network 15.

Also in the blood state evaluation system according to the present embodiment, since the state of blood is evaluated on the basis of chronological change data of the electrical characteristic, a simple blood test enables evaluation of the thrombosis risk highly precisely.

Additionally, the present technology may also be configured as below.

(1)

A blood state evaluation device including at least:

an evaluation unit configured to evaluate a state of blood on the basis of chronological change data of an electrical characteristic of the blood in two or more frequencies or frequency bands.

(2)

The blood state evaluation device according to (1), wherein the evaluation unit extracts at least one feature point from the chronological change data of the electrical characteristic.

(3)

The blood state evaluation device according to (2), wherein the at least one feature point is a change amount $\delta E\ (=E(f_x,t_y)/E(f_x,t_a))$ in an electrical characteristic value E in a given frequency $f_x$ from a reference time $t_a$ to a given time $t_y$.

(4)

The blood state evaluation device according to (1), wherein the evaluation unit digitalizes the chronological change data of the electrical characteristic.

(5)

The blood state evaluation device according to (4), wherein the evaluation unit evaluates the state of the blood by comparing a determination value calculated from the chronological change data of the electrical characteristic with a predetermined threshold.

(6)

The blood state evaluation device according to (1), wherein the evaluation unit evaluates the state of the blood by an increase and/or a decrease in an electrical characteristic value E in a given frequency $f_x$ on the basis of the chronological change data of the electrical characteristic.

(7)

The blood state evaluation device according to any one of (1) to (6), wherein the electrical characteristic is at least one kind of values selected from impedance, conductance, admittance, capacitance, permittivity, conductivity, phase angle, and a quantity obtained by conversing such a value into a quantity of electricity.

(8)

The blood state evaluation device according to any one of (1) to (7), wherein the evaluation unit evaluates a coagulation state of the blood.

(9)

The blood state evaluation device according to any one of (1) to (8), further including:

a measurement unit configured to chronologically measure the electrical characteristic of blood being an evaluation target, in a particular frequency or frequency band.

(10)

A blood state evaluation system including:

an electrical characteristic measurement device including a measurement unit that chronologically measures an electrical characteristic of blood being an evaluation target, in a particular frequency or frequency band; and a blood state evaluation device including an evaluation unit that evaluates a state of the blood on the basis of chronological change data in two or more frequencies or frequency bands from among electrical characteristics measured by the electrical characteristic measurement device.

(11)

The blood state evaluation system according to (10) further including:

a server including an information storage unit that stores a result of measurement in the permittivity measurement device and/or a result of evaluation in the blood state evaluation device, wherein the server is connected to the permittivity measurement device and/or the blood state evaluation device through a network.

(12)

A blood state evaluation method including:

an electrical characteristic measurement step of chronologically measuring an electrical characteristic of blood being an evaluation target in a particular frequency or frequency band; and a blood state evaluation step of evaluating a state of the blood on the basis of chronological change data in two or more frequencies or frequency bands from among electrical characteristics measured in the electrical characteristic measurement step.

(13)

A program for causing a computer to execute:

an evaluation function of evaluating a state of blood on the basis of chronological change data of an electrical characteristic of the blood in two or more frequencies or frequency bands.

EXAMPLES

Hereinafter, effects of the present disclosure will be specifically described. In the present example, the thrombosis risk was evaluated using the blood state evaluation device according to the above-described first embodiment by the following method.

Example 1

Experimental Method

Using a vacuum blood collection tube in which sodium citrate was treated as an anti-coagulant agent, blood was collected in the following morning of surgery (before medication starts after surgery). The temperature of the specimen blood was kept at 37° C. in advance, and 0.25 M of an aqueous solution of calcium chloride was added to the specimen blood at a concentration of 85 μL per 1 mL of blood immediately before the start of measurement, to initiate a blood coagulation reaction.

Figure 5:
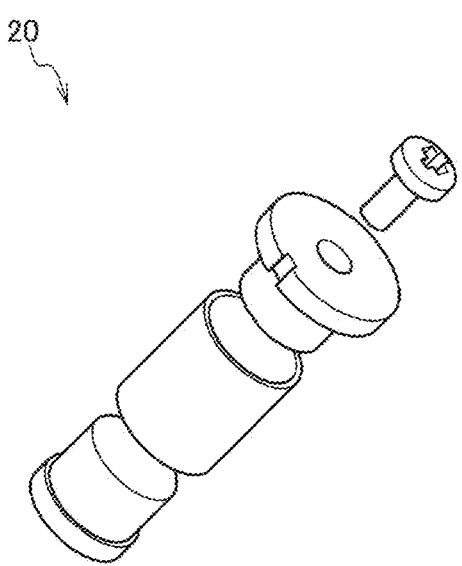
FIG. 5 is a diagram illustrating a configuration of a sample container used in Examples.

Then, dielectric measurement (impedance measurement) was performed for a blood coagulation process of the specimen blood using a dielectric coagulometry prototype machine available from Sony Corporation. The measurement was performed under the conditions of a measurement temperature of 37° C., a measurement frequency range of 100 Hz to 40 MHz, a measurement interval of one minute, and a measurement time of 60 minutes. A sample container 20 illustrated in FIG. 5 was used for the measurement. In order to reduce the influence of blood sedimentation, the measurement was performed by rotating the sample container 20 once a minute by 180°.

On the fourth or fifth day from the surgery, it was checked whether venous thromboembolism (VTE) occurred. Specifically, deep vein thrombosis (DVT) was checked by ultrasonography, and pulmonary embolism (PE) was checked by computed tomography (CT).

<Image Diagnosis>

As a result of image diagnosis by ultrasonography and computed tomography (CT), 21 examples were positive for venous thromboembolism (VTE) and 9 examples were negative for venous thromboembolism (VTE) out of 30 examples investigated.

<Dielectric Blood Coagulation Time>

The dielectric blood coagulation time was calculated from a change in permittivity in 10 MHz. The dielectric blood coagulation time of blood positive for venous thromboembolism (VTE) was 23±5 minutes, and the dielectric blood coagulation time of blood negative for venous thromboembolism (VTE) was 20±4 minutes. Each of these values was shorter than the value of blood of a healthy person, which was 40±6 minutes, and accordingly was confirmed to be in a state of enhanced blood coagulability having a high thrombosis risk. However, the prediction only by the dielectric blood coagulation time as to whether venous thromboembolism (VTE) occurs in reality at a high sensitivity and a high specificity was found to be difficult.

<Evaluation Using Determination Value $p_1$>

Next, the determination value $p_1$ was calculated using the above-described formula 1. In this event, $f_1$=2.5 kHz, $f_2$=1 MHz, $f_3$=10 MHz, $t_1$=$t_3$−5 min, and $t_2$=18 min. Note that $t_3$ is the dielectric blood coagulation time. The threshold was set to 0.765, and the determination value $p_1$ being smaller than this value was determined to be "positive". The results are shown below in Table 1.

TABLE 1

| | | True State | | |
|---|---|---|---|---|
| | | Positive | Negative | |
| Test Results | Positive | True Positive 19 | False Positive 2 | Positive Predictive Value 90% |
| | Negative | False Negative 2 | True Negative 7 | Negative Predictive Value 78% |
| | | Sensitivity 90% | Specificity 78% | |

As illustrated in Table 1, this method enables evaluation of the thrombosis risk at a satisfactory score of a sensitivity being 90% and a specificity being 78%.

Here, the "sensitivity" and the "specificity" are indexes used in laboratory tests. Specifically, the "sensitivity" is a value defined as the "possibility at which an object that is supposed to be determined to be positive is correctly determined to be positive", and the "specificity" is the "possibility at which an object that is negative is correctly determined to be negative". In addition, it is preferable that each of these values is high, and a method by which high values are obtained for both the "sensitivity" and the "specificity" is an excellent testing method. However, when setting a threshold, a priority to the sensitivity results in a lower specificity, whereas a priority to the specificity results in a lower sensitivity. Accordingly, the threshold is typically set in a manner that both values can be within acceptable ranges.

Example 2

Next, as in the method described in Example 1, the thrombus risk of specimen blood (the number of specimens was 27) was evaluated using the determination value $p_2$ of the above-described formula 2. In this event, $f_1=2.5$ kHz, $f_2=1$ MHz, $f_3=10$ MHz, $a=0.67$, and $t_1=t_2=t_3$ being the dielectric blood coagulation time. The threshold was set to 0.11, and the determination value $p_2$ being smaller than this value was determined to be "positive". The results are shown below in Table 2.

TABLE 2

| | | True State | | |
|---|---|---|---|---|
| | | Positive | Negative | |
| Test Results | Positive | True Positive 7 | False Positive 3 | Positive Predictive Value 70% |
| | Negative | False Negative 1 | True Negative 16 | Negative Predictive Value 94% |
| | | Sensitivity 88% | Specificity 84% | |

As illustrated in Table 2, this method enables evaluation of pulmonary embolism (PE) at a satisfactory score of a sensitivity being 88% and a specificity being 84%.

Example 3

Next, as in the method described in Example 1, the thrombus risk of specimen blood (the number of specimens was 30) was evaluated using the determination value $p_3$ of the above-described formula 3. In this event, $f_1=2.5$ kHz, $f_2=10$ MHz, $t_1=t_2=6$ min, and $t_2$ was the dielectric blood coagulation time. The threshold was set to 0.765, and the determination value $p_3$ being smaller than this value was determined to be "positive". The results are shown below in Table 3.

TABLE 3

| | | True State | | |
|---|---|---|---|---|
| | | Positive | Negative | |
| Test Results | Positive | True Positive 18 | False Positive 3 | Positive Predictive Value 86% |
| | Negative | False Negative 3 | True Negative 6 | Negative Predictive Value 67% |
| | | Sensitivity 86% | Specificity 67% | |

As illustrated in Table 3, this method enables evaluation of the thrombosis risk at a satisfactory score of a sensitivity being 86% and a specificity being 67%.

Example 4

In Example 4, measurement was performed using venous blood of a patient with diabetes and a patient with both diabetes and a collagen disease. In this event, a vacuum blood collection tube in which sodium citrate was treated as an anti-coagulant agent was used to collect blood. The temperature of the specimen blood was kept at 37° C. in advance, and 0.25 M of an aqueous solution of calcium chloride was added to the specimen blood at a concentration of 85 μL per 1 mL of blood immediately before the start of measurement, to initiate a blood coagulation reaction. The measurement was performed under the conditions of a measurement temperature of 37° C., a measurement frequency range of 40 Hz to 110 MHz, a measurement interval of two minutes, and a measurement time of 60 minutes.

Figure 6:
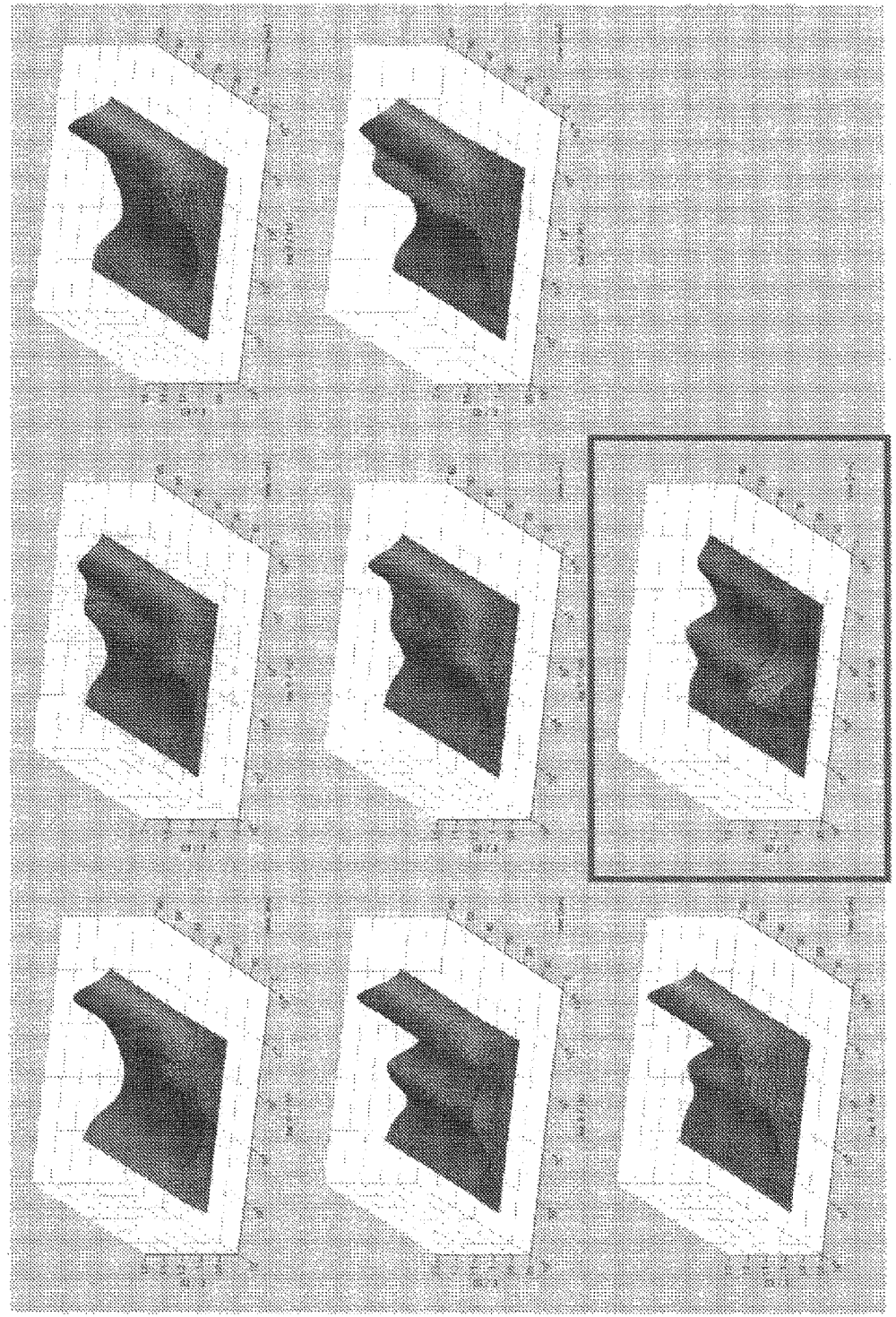
FIG. 6 is chronological change data of permittivity (change amounts $\delta\varepsilon$ in real parts of complex permittivity) of blood of a patient with diabetes, measured in Example 4.
Figure 7A:
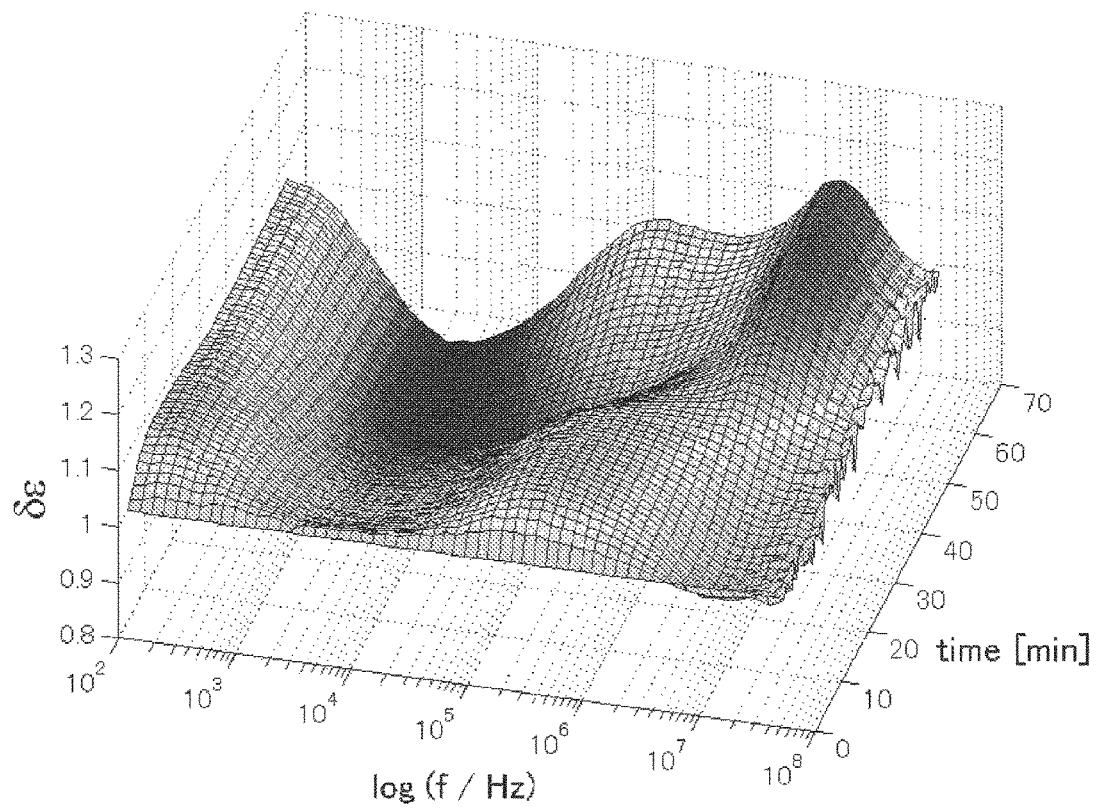
FIG. 7A is chronological change data of permittivity (change amount $\delta\varepsilon$ of a real part of complex permittivity of a blood specimen within a normal value measured in Example 5.
Figure 7B:
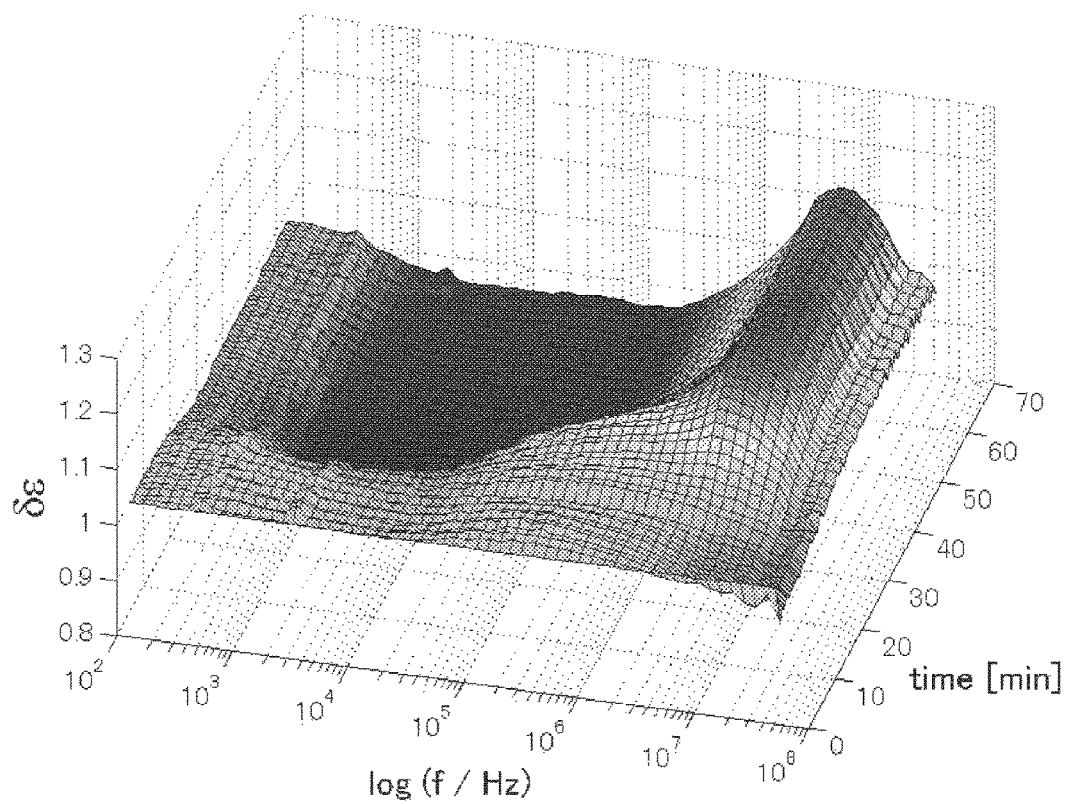
FIG. 7B is chronological change data of permittivity (change amount $\delta\varepsilon$ of a real part of complex permittivity of a blood specimen within a normal value measured in Example 5.
Figure 7C:
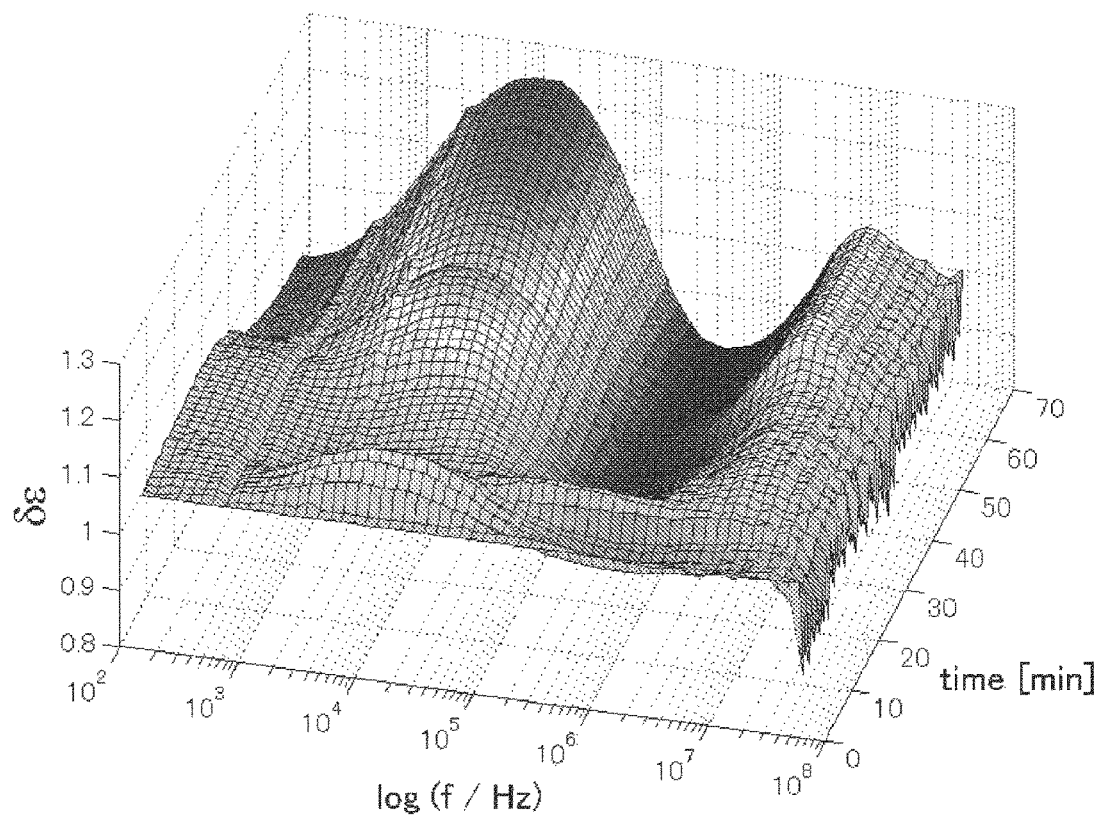
FIG. 7C is chronological change data of permittivity (change amount $\delta\varepsilon$ of a real part of complex permittivity of a blood specimen having an abnormal value measured in Example 5.
Figure 7D:
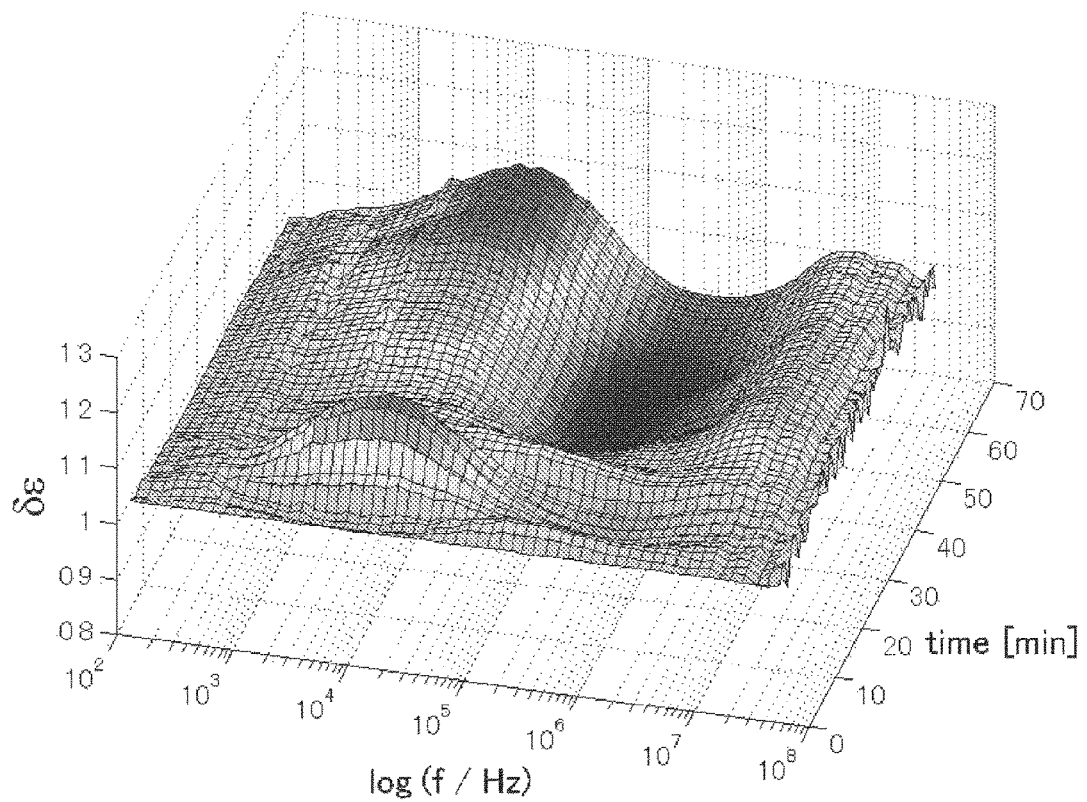
FIG. 7D is chronological change data of permittivity (change amount $\delta\varepsilon$ of a real part of complex permittivity of a blood specimen having an abnormal value measured in Example 5.

FIG. 6 is chronological change data of permittivity (change amounts δε in real parts of complex permittivity) of blood of the patient with diabetes. Data surrounded by a thick line in FIG. 6 was of blood of the patient with a collagen disease, and has a different pattern from other data obviously. Specifically, as for the patient with a collagen disease, permittivity rapidly increases and then decreases in a frequency band from 1 to 100 kHz in 20 minutes immediately after the start of measurement. Note that such a feature is not seen in the patient with diabetes who did not have a collagen disease or a healthy person. The use of this method was confirmed to enable evaluation as to whether a collagen disease occurred, at the blood test.

Example 5

In Example 5, measurement was performed using venous blood that was collected before surgery of a patient who was supposed to undergo artificial knee joint replacement. In this event, a vacuum blood collection tube in which sodium citrate was treated as an anti-coagulant agent was used to collect blood. The temperature of the specimen blood was kept at 37° C. in advance, and 0.25 M of an aqueous solution of calcium chloride was added to the specimen blood at a concentration of 85 μL per 1 mL of blood immediately before the start of measurement, to initiate a blood coagulation reaction. The measurement was performed under the conditions of a measurement temperature of 37° C., a measurement frequency range of 100 Hz to 40 MHz, a measurement interval of one minute, and a measurement time of 60 minutes.

The resulting data was compared with an erythrocyte sedimentation rate (ESR), which is one of general values for blood test. A normal value of the erythrocyte sedimentation rate is 10 mm/60 min for men or 15 mm/60 min for women. As a result, an obvious relation was found between these values and a dielectric coagulation pattern, and the dielectric measurement was confirmed to be able to evaluate the erythrocyte sedimentation rate.

FIGS. 7A to 7D are chronological change data of permittivity (change amounts $\delta\varepsilon$ of real parts of complex permittivity of blood within normal values (A and B) and of blood having abnormal values (C and D). Erythrocyte sedimentation rates of blood specimens of FIGS. 7A to 7D are illustrated below in Table 4. As illustrated in FIGS. 7A to 7D, the blood specimens within normal values and the blood specimens having abnormal values have significantly different features in a frequency band of 1 to 30 kHz. In a case of the erythrocyte sedimentation rate being a normal value, $\delta\varepsilon$ is a low value on a long-time side in a frequency band of 1 to 30 kHz in association with blood coagulation. In contrast, in a case of the erythrocyte sedimentation rate being an abnormal value, $\delta\varepsilon$ is a high value on a long-time side in a frequency band of 1 to 30 kHz. The use of this method was confirmed to enable evaluation of abnormality of the erythrocyte sedimentation rate.

TABLE 4

| Specimen | Erythrocyte Sedimentation Rate (mm/60 min) |
|---|---|
| A | 2 |
| B | 6 |
| C | 84 |
| D | 56 |

REFERENCE SIGNS LIST 1 blood state evaluation device
2 measurement unit
3 evaluation unit
4 storage unit
5 display unit
11 electrical characteristic measurement device
12 information processing device
13 server
14 display device
15 network
20 sample container

The invention claimed is:

1. A blood state evaluation device comprising at least:
a pair of electrodes provided in a sample container configured to be filled with blood, the pair of electrodes configured to apply an alternating voltage therebetween; and
at least one programmed processor operatively coupled to the pair of electrodes, the at least one programmed processor configured to:
chronologically measure an electrical characteristic of blood being an evaluation target, in two or more frequencies or frequency bands using the pair of electrodes; and
evaluate a state of the blood on the basis of chronological change data in the two or more frequencies or frequency bands for the measured electrical characteristic.

2. The blood state evaluation device according to claim 1, wherein the evaluation unit is configured to extract at least one feature point from the chronological change data of the electrical characteristic.

3. The blood state evaluation device according to claim 2, wherein the at least one feature point is a change amount $\delta E(=E(f_x,t_y)/E(f_x,t_a))$ in an electrical characteristic value E in a given frequency $f_x$ from a reference time $t_a$ to a given time $t_y$.

4. The blood state evaluation device according to claim 1, wherein the evaluation unit is configured to digitize the chronological change data of the electrical characteristic.

5. The blood state evaluation device according to claim 4, wherein the evaluation unit is configured to evaluate the state of the blood by comparing a determination value calculated from the chronological change data of the electrical characteristic with a predetermined threshold.

6. The blood state evaluation device according to claim 1, wherein the evaluation unit is configured to evaluate the state of the blood by an increase and/or a decrease in an electrical characteristic value E in a given frequency $f_x$ on the basis of the chronological change data of the electrical characteristic.

7. The blood state evaluation device according to claim 1, wherein the electrical characteristic is at least one kind of value selected from impedance, conductance, admittance, capacitance, permittivity, conductivity, phase angle, and a quantity obtained by conversing such a value into a quantity of electricity.

8. The blood state evaluation device according to claim 1, wherein the evaluation unit is configured to evaluate a coagulation state of the blood.

9. A blood state evaluation system comprising:
an electrical characteristic measurement device comprising a pair of electrodes provided in a sample container configured to be filled with blood, the electrical characteristic measurement device configured to:
apply an alternating voltage between the pair of electrodes; and
chronologically measure an electrical characteristic of blood being an evaluation target, in two or more frequencies or frequency bands using the pair of electrodes; and
a blood state evaluation device operatively coupled to the electrical characteristic measurement device, the blood state evaluation device comprising at least one programmed processor configured to evaluate a state of the blood on the basis of chronological change data in the two or more frequencies or frequency bands for the measured electrical characteristic.

10. The blood state evaluation system according to claim 9 further comprising:
a server including an information storage unit configured to store a result of measurement in a permittivity measurement device and/or a result of evaluation in the blood state evaluation device, wherein the server is connected to the permittivity measurement device and/or the blood state evaluation device through a network.

11. A blood state evaluation method comprising:

applying an alternating voltage between a pair of electrodes provided in a sample container configured to be filled with blood;

at least one programmed processor operatively coupled to the pair of electrodes, the at least one programmed processor:

chronologically measuring an electrical characteristic of blood being an evaluation target in two or more frequencies or frequency bands using the pair of electrodes; and evaluating a state of the blood on the basis of chronological change data in the two or more frequencies or frequency bands for the measured electrical characteristic.

12. A blood state evaluation method comprising:

Applying an alternating voltage between a pair of electrodes provided in a sample container configured to be filled with blood;

At least one programmed processor operatively coupled to the pair of electrodes, the at least one programmed processor configured to:

Chronologically measure an electrical characteristic of blood being an evaluation target in two or more frequencies or frequency bands using the pair of electrodes; and Evaluate a state of the blood on the basis of chronological change data in the two or more frequencies or frequency bands for the measure electrical characteristics.

* * * * *